(12) United States Patent  
Ito et al.

(10) Patent No.: US 7,547,503 B2
(45) Date of Patent: Jun. 16, 2009

(54) PHOTOSENSITIVE SILANE COUPLING AGENT, METHOD OF FORMING PATTERN, AND METHOD OF FABRICATING DEVICE

(75) Inventors: Toshiki Ito, Kawasaki (JP); Natsuhiko Mizutani, Tokyo (JP); Takako Yamaguchi, Kawasaki (JP); Yasuhisa Inao, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 164 days.

(21) Appl. No.: 11/710,901

(22) Filed: Feb. 27, 2007

(65) Prior Publication Data

US 2007/0218373 A1 Sep. 20, 2007

(30) Foreign Application Priority Data

Mar. 14, 2006 (JP) .............................. 2006-070002

(51) Int. Cl.
*G03F 7/20* (2006.01)
*G03F 7/26* (2006.01)
*G03F 7/36* (2006.01)
*C07F 7/10* (2006.01)

(52) U.S. Cl. ..................... 430/311; 430/313; 430/315; 430/319; 430/320; 430/321; 430/322; 430/323; 430/324; 430/325; 430/326; 430/327; 430/331; 430/270.1; 430/5; 556/420; 556/422

(58) Field of Classification Search ....................... None
See application file for complete search history.

(56) References Cited

U.S. PATENT DOCUMENTS 5,692,003 A    11/1997  Wingreen et al.  ............. 372/50

| 6,755,953 | B2 | 6/2004 | Baba | 205/74 |
| 7,022,463 | B2 | 4/2006 | Yamaguchi et al. | 430/291 |
| 7,079,250 | B2 | 7/2006 | Mukai | 356/445 |
| 7,204,915 | B2 | 4/2007 | Kitade et al. | 204/192.2 |
| 7,220,482 | B2 | 5/2007 | Mino et al. | 428/403 |
| 2004/0223142 | A1 | 11/2004 | Inao et al. | 356/237.1 |
| 2007/0059211 | A1* | 3/2007 | Edmiston | 422/82.11 |
| 2007/0141483 | A1 | 6/2007 | Yamaguchi et al. | 430/5 |
| 2007/0212806 | A1 | 9/2007 | Ito | 438/99 |

FOREIGN PATENT DOCUMENTS

JP          10-12968         1/1998

(Continued)

OTHER PUBLICATIONS

Aránzazu del Campo, et al., "Surface Modification with Orthogonal Photosensitive Silanes for Sequential Chemical Lithography and Site-Selective Particle Deposition", Angew. Chem. Int. Ed., vol. 44, 2005, pp. 4707-4712.

Jamila Jennane, et al, "Photolithography of self-assembled monolayers: optimization of protecting groups by an electroanalytical method", Can. J. Chem., vol. 74, 1996, pp. 2509-2517.

(Continued)

*Primary Examiner*—Sin J. Lee
(74) *Attorney, Agent, or Firm*—Fitzpatrick, Cella, Harper & Scinto

(57) ABSTRACT

Provided is a photosensitive silane coupling agent for forming a low-defect microparticle pattern, dot array pattern, or hole array pattern with a smaller number of process steps, and a method of forming a pattern using such photosensitive silane coupling agent. Used is a photosensitive silane coupling agent having a secondary amino group protected by an o-nitrobenzyloxycarbonyl group.

14 Claims, 4 Drawing Sheets

FORMATION OF A PHOTOSENSITIVE
SILANE COUPLING AGENT LAYER

FOREIGN PATENT DOCUMENTS

| | | |
|---|---|---|
| JP | 11-218627 | 8/1999 |
| JP | 2001-168317 | 6/2001 |
| JP | 2003-168606 | 6/2003 |
| JP | 2003-268592 | 9/2003 |
| JP | 2003-321479 | 11/2003 |
| JP | 2005-190624 | 7/2005 |

OTHER PUBLICATIONS

Takashi Tamura, et al., "Synthesis of mesoporous thin film containing 2-nitrobenzyl group and introduction of carboxy groups patterned on the surface by photoirradiation", Polymer Preprints, Japan, vol. 53, No. 2, 2004, p. 4196. (with translation).

* cited by examiner

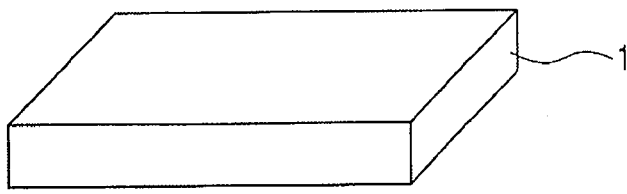
FIG. 1A
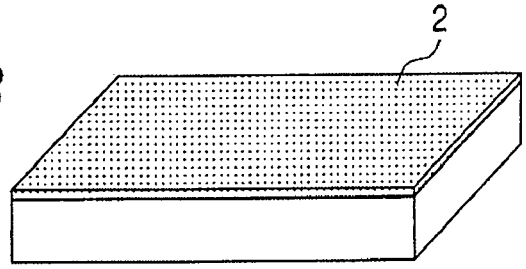
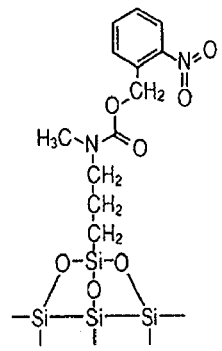
FIG. 1B
FIG. 1C
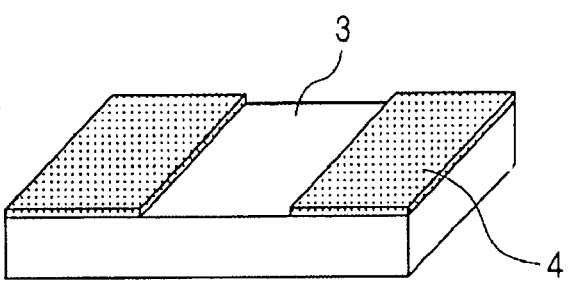
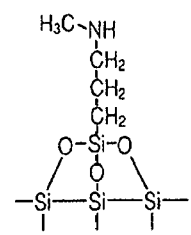
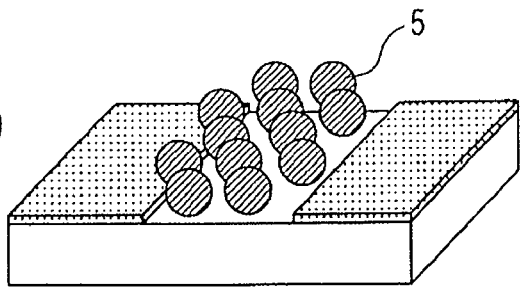
FIG. 1D

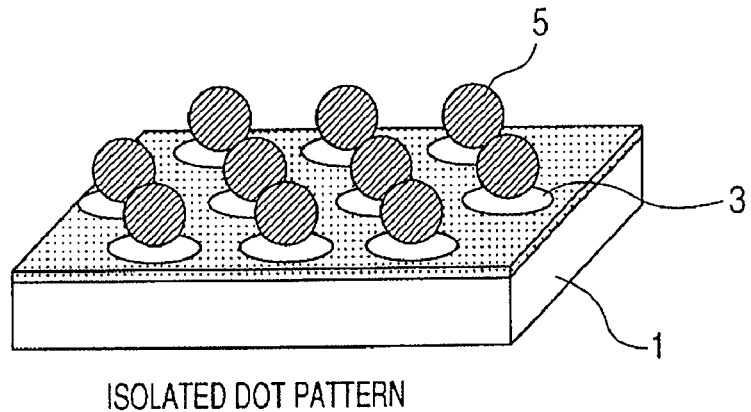
FIG. 2A  ISOLATED DOT PATTERN
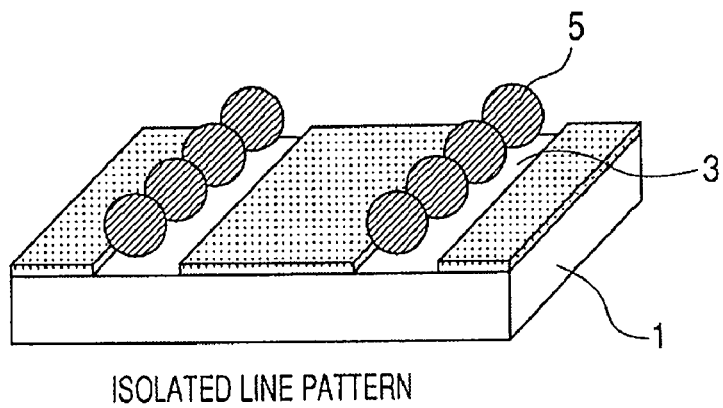
FIG. 2B  ISOLATED LINE PATTERN
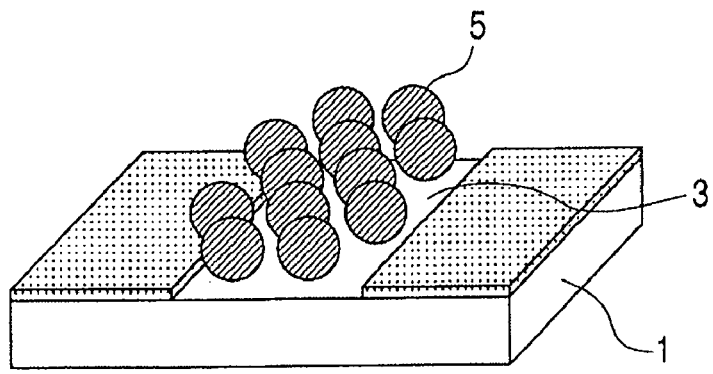
FIG. 2C  CLOSEST PACKED PATTERN
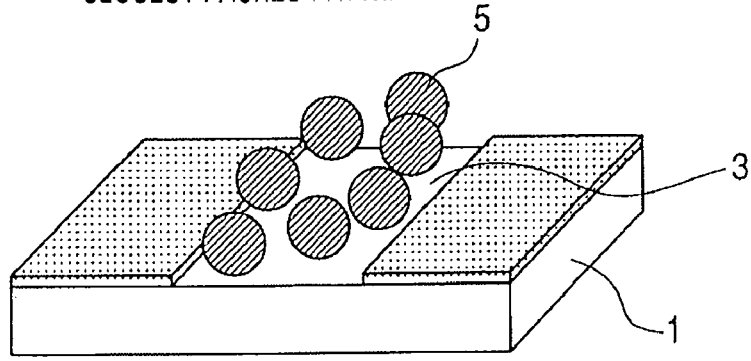
FIG. 2D  RANDOM PATTERN

↓ ETCHING

↓ FILM FORMATION

↓ LIFT OFF

PHOTOSENSITIVE SILANE COUPLING AGENT, METHOD OF FORMING PATTERN, AND METHOD OF FABRICATING DEVICE

BACKGROUND OF THE INVENTION

1. Field of the Invention

The present invention relates to a photosensitive silane coupling agent, a method of forming a pattern using the photosensitive silane coupling agent, and a method of fabricating a device.

2. Description of the Related Art

Recently, in the fields of various electronic devices which require microfabrication, such as semiconductor devices, there has been ever increasing demands for increased density and integration of the devices.

In the step of fabricating a semiconductor device, it is the photolithography process that plays an important part in forming the fine circuit pattern.

Most current photolithography processes are carried out by reduced projection exposure. However, the resolution of reduced projection exposure is limited by the light diffraction limit, which is about one-third the wavelength of the light source. Thus, attempts have been made to achieve shorter wavelengths using techniques such as employing an excimer laser as the exposure light source, whereby microfabrication at about 100 nm level is now possible.

Thus, although photolithography continues to have improving fineness, many problems needing to be resolved have arisen, such as the increased size of the equipment resulting from shortening the wavelength of the light source, as well as development of lenses for such wavelength region, equipment costs and costs of the corresponding resist.

Further, devices have recently been proposed which require a high-density hole array pattern or dot array pattern. Specific examples include a single-electron device (Japanese Patent Application Laid-Open No. 2001-168317), patterned media (Japanese Patent Application Laid-Open No. 2005-190624), a chemical sensor (Japanese Patent Application Laid-Open No. 2003-268592), a quantum dot laser element (Japanese Patent Application Laid-Open No. H10-012968), and a photonic crystal optical device (Japanese Patent Application Laid-Open No. H11-218627).

However, because these devices require even greater high-precision microfabrication techniques than those for semiconductor devices, mass production has been difficult with conventional photolithography techniques.

On the other hand, as a low-cost and simple method for forming a micropattern that can take the place of the lithography techniques, methods have been reported which cause the microparticles to arrange in a self-organizing manner.

Further, in recent years methods have also been proposed for forming a micropattern by forming chemically reactive groups in a pattern on a substrate surface using an energy beam and then utilizing the interaction between the chemically reactive groups and the microparticles. Specific examples are disclosed in Polymer Preprints, Japan, Japanese Ed., Vol. 53, 4196 (2004) and Japanese Patent Application Laid-Open No. 2003-168606.

These examples are technologies which fuse lithography and self-organization. In the present invention such technologies will be referred to as "build-up lithography".

Polymer Preprints, Japan, Japanese Ed., Vol. 53, 4196 (2004) discloses a method in which a monomolecular film of a photosensitive silane coupling agent is exposed to a light, and then microparticles are made to adhere to the exposed portion. Specifically, in the method disclosed, a photosensitive silane coupling agent having a carboxyl group which is protected by a nitrobenzyl group is irradiated with UV rays to thereby form a carboxyl group on the irradiated portion, and the resultant object is dipped in an aqueous solution of fluorescent microparticles for selectively making the fluorescent microparticles adhere to the exposed portion.

Japanese Patent Application Laid-Open No. 2003-168606 discloses the results of examples in which a monomolecular film of a photosensitive silane coupling agent having an unsaturated alkyl group was irradiated with X-rays in a pattern to excite the unsaturated bonds in the exposed portion, whereby bonds were formed with the organic film on the surface of the metal microparticles.

As with the above-described prior examples, in build-up lithography a photosensitive silane coupling agent is employed which forms a chemically reactive group upon the light irradiation.

In addition, in "Buildup Photolithography" in the proceedings of the fourth NIMS International Symposium on Photoreaction Control and Photofunctional Materials, March, 2001, a photosensitive silane coupling agent is disclosed which forms a primary amine.

The photosensitive silane coupling agent disclosed in the "Buildup Photolithography" has a structure in which the primary amino group of a primary-amino-containing silane coupling agent is protected by an O-nitrobenzyloxycarbonyl group. The protected amino group forms a primary amino group by a photoreaction such as that represented by the following chemical formula, and an o-nitrosobenzaldehyde is simultaneously formed as a byproduct.

As illustrated in the following chemical formula, it is known that aldehyde compounds will react with a primary amine to form an imine compound. Specifically, the primary amine formed on the exposed portion is eliminated, whereby the contrast in chemical reactivity between the exposed portion and the unexposed portion is reduced, so that in some cases defects may form in the microparticle pattern.

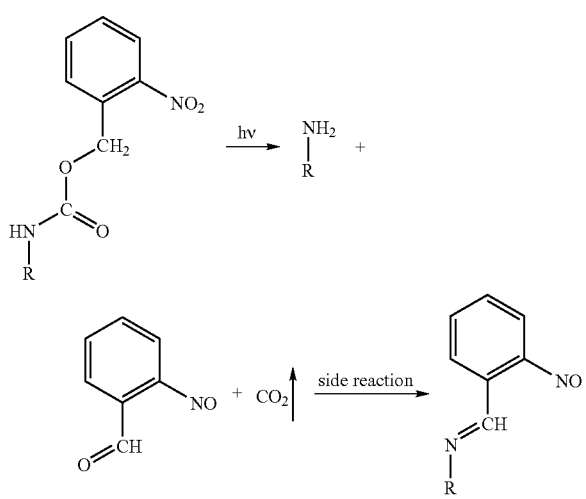

In order to prevent the side reaction in the above reaction formula to form a microparticle pattern which has few defects, it is necessary to carry out a rinsing step for removing the nitrosobenzaldehyde as the byproducts. For mass production of a device, from the perspective of costs, a smaller number of steps is preferable.

SUMMARY OF THE INVENTION

The photosensitive silane coupling agent provided by the present invention comprises a structure represented by the following general formula (1):

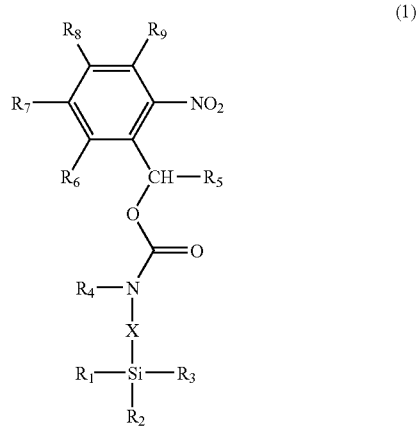

wherein X is a polymethylene group part of hydrogen atoms of which may be substituted with a fluorine atom or an alkyl group, a phenylene group part of hydrogen atoms of which may be substituted with a fluorine atom or an alkyl group, a naphthylene group part of hydrogen atoms of which may be substituted with a fluorine atom or an alkyl group, or a divalent group having a structure on which at least two of these divalent groups are bonded to each other; at least one of $R_1$, $R_2$ and $R_3$ is an alkoxy group or a halogen atom, the other(s) being selected from the group consisting of an alkyl group, an alkenyl group and a hydrogen atom; $R_4$ is an alkyl group part of hydrogen atoms of which may be substituted with a fluorine atom, a phenyl group part of hydrogen atoms of which may be substituted with a fluorine atom or an alkyl group, or a naphthyl group part of hydrogen atoms of which may be substituted with a fluorine atom or an alkyl group; $R_5$ is a hydrogen atom or an alkyl group; and $R_6$, $R_7$, $R_8$ and $R_9$ are selected from the group consisting of a nitro group, a hydrogen atom, a halogen atom, an alkyl group, and an alkyl group or an alkoxy group part or the whole of hydrogen atoms of which are substituted with a fluorine atom.

The method of forming the pattern provided by the present invention forms a pattern having a structure wherein a plurality of microparticles which have an average particle diameter of at least 0.5 nm and at most 500 nm are arranged on a substrate, the method comprising the steps of: layering the photosensitive silane coupling agent according to the present invention onto a surface of the substrate, exposing the photosensitive silane coupling agent layer patternwise, generating a carboxyl group on the photosensitive silane coupling agent in the exposed portion, and selectively arranging microparticles on the exposed portion or unexposed portion.

The method according to the present invention also encompasses a method comprising the step of processing the substrate by etching with the microparticle pattern as a mask.

The method according to the present invention also encompasses a method comprising the steps of forming a film over the entire substrate on which the microparticle pattern is formed, and forming a film pattern by removing the microparticle pattern and the film formed thereon.

The method according to the present invention also encompasses a method comprising arrangement of the microparticles using a colloidal solution containing the microparticles.

The present invention also encompasses a method comprising carrying out the exposure to near-field light generated from an exposure mask which is provided with a light-shielding layer comprising an opening narrower than the wavelength of the exposure light source.

The present invention also encompasses a method where the microparticles are formed of a material selected from the group consisting of metals, metal oxides, semiconductors and resins.

The present invention also encompasses a method where the microparticles have an amino group on an end of the surface of the microparticles.

The present invention also encompasses a method of fabricating a device using the method of forming a pattern according to the present invention.

The method of fabricating a device according to the present invention also encompasses a method comprising fabrication of a single-electron device by forming minute tunnel junction sites using the method of forming a pattern according to the present invention.

The method of fabricating a device according to the present invention also encompasses a method comprising fabrication of a patterned medium by forming a magnetic bit array using the method of forming a pattern according to the present invention.

The method of fabricating a device according to the present invention also encompasses a method comprising fabrication of a chemical sensor by forming a metallic microparticle pattern using the method of forming a pattern according to the present invention.

The method of fabricating a device according to the present invention also encompasses a method comprising fabrication of a quantum dot laser element by forming a quantum dot array structure using the method of forming a pattern according to the present invention.

The method of fabricating a device according to the present invention also encompasses a method comprising fabrication of a photonic crystal optical device by forming a two-dimensional photonic crystal structure using the method of forming a pattern according to the present invention.

Further features of the present invention will become apparent from the following description of exemplary embodiments with reference to the attached drawings.

BRIEF DESCRIPTION OF THE DRAWINGS

FIGS. 1A, 1B, 1C and 1D are a process chart illustrating one embodiment of a method for forming a pattern using the photosensitive silane coupling agent according to the present invention.

FIGS. 2A, 2B, 2C and 2D are a schematic diagram illustrating a pattern formed by selectively arranging microparticles only on an exposed portion or an unexposed portion.

DESCRIPTION OF THE EMBODIMENTS

Figure 3:
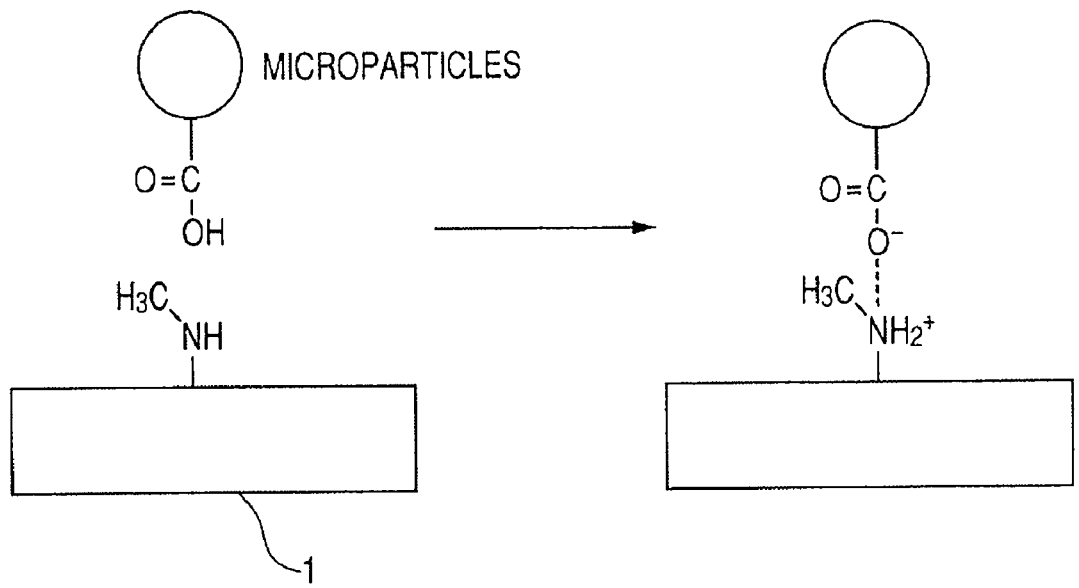
FIG. 3 is an explanatory diagram illustrating the bonding between a secondary amine group of the exposed portion of the substrate and a carboxyl group on the surface end of the microparticle.

The present invention will now be described in more detail.

The photosensitive silane coupling agent according to the present invention has a structure represented by the following general formula (1).

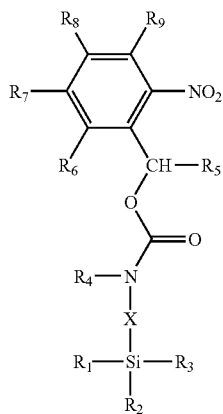

(1)

In the formula, X is a polymethylene group part of hydrogen atoms of which may be substituted with a fluorine atom or an alkyl group, a phenylene group part of hydrogen atoms of which may be substituted with a fluorine atom or an alkyl group, a naphthylene group part of hydrogen atoms of which may be substituted with a fluorine atom or an alkyl group, or a divalent group having a structure on which at least two of these divalent groups are bonded to each other.

The polymethylene group is represented by $-(CH_2)_n-$, wherein n denotes an integer of from 1 to 10, and preferably denotes an integer of from 1 to 5.

At least one of $R_1$, $R_2$ and $R_3$ is an alkoxy group or a halogen atom, the other(s) being selected from the group consisting of an alkyl group, an alkenyl group and a hydrogen atom.

$R_4$ is an alkyl group part of hydrogen atoms of which may be substituted with a fluorine atom, a phenyl group part of hydrogen atoms of which may be substituted with a fluorine atom or an alkyl group, or a naphthyl group part of hydrogen atoms of which may be substituted with a fluorine atom or an alkyl group.

$R_5$ is a hydrogen atom or an alkyl group.

$R_6$, $R_7$, $R_8$ and $R_9$ are selected from the group consisting of a nitro group, a hydrogen atom, a halogen atom, an alkyl group, and an alkyl group or an alkoxy group part or the whole of hydrogen atoms of which are substituted with a fluorine atom.

The photosensitive silane coupling agent according to the present invention has a secondary amino group which is protected by an o-nitrobenzyloxycarbonyl group. As shown in the following chemical formula, the photosensitive silane coupling agent is decomposed by UV irradiation, and a secondary amino group is regenerated.

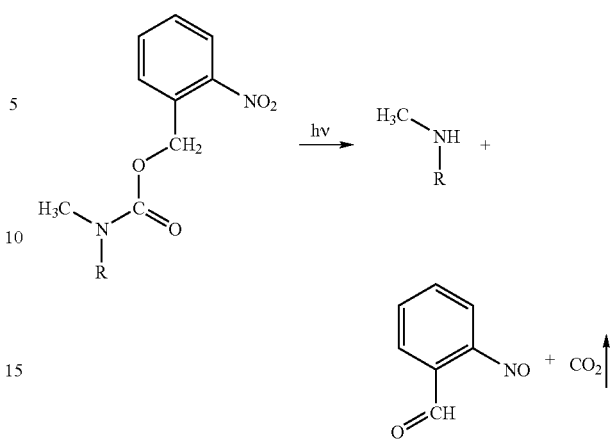

The method of synthesizing the photosensitive silane coupling agent according to the present invention will now be described in detail.

As shown in the following chemical formula, the photosensitive silane coupling agent according to the present invention can be obtained by reacting at room temperature 2-nitrobenzyl chloroformate or 4,5-dimethoxy-2-nitrobenzyl chloroformate with a silane coupling agent having a secondary amine. The reaction is carried out in the presence of a tertiary amine such as triethylamine, dimethylaminopyridine or the like. The 2-nitrobenzyl chloroformate, 4,5-dimethoxy-2-nitrobenzyl chloroformate, triethylamine and dimethylaminopyridine are all available commercially. Specific examples of the silane coupling agent having a secondary amine include, but are not limited to, products which can be acquired commercially such as N-methylaminopropyltrimethoxysilane, N-methylaminopropyl-methyldimethoxysilane and N-ethylaminoisobutyl-trimethoxysilane.

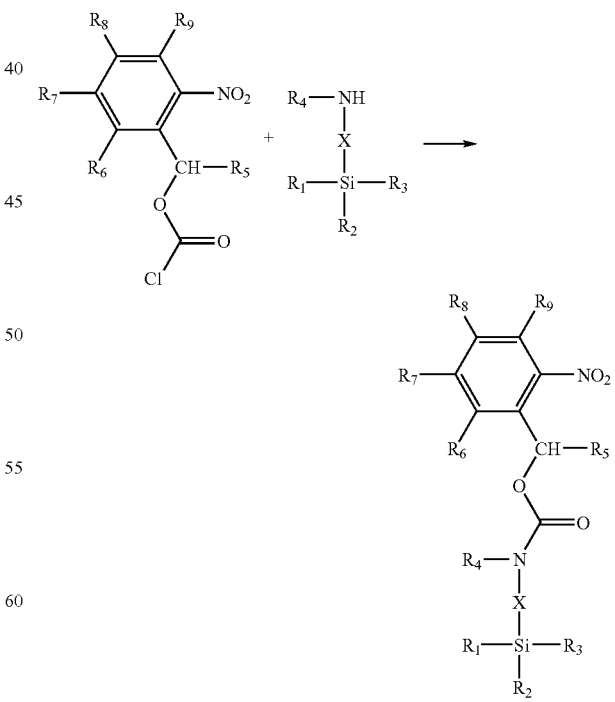

In the formula, X and $R_1$ to $R_9$ have the same meaning as that defined in formula (1).

According to the present invention, a photosensitive silane coupling agent is provided which can form by build-up lithography a pattern having few defects without requiring a rinsing step or a photolithography step that utilizes a resist.

The present invention also provides a method of forming a pattern using such photosensitive silane coupling agent. In addition, the present invention also provides a method of fabricating various devices, such as a single-electron device, patterned media, a chemical sensor, a quantum dot laser element and a photonic crystal optical device.

EXAMPLE

The method of forming a pattern using the photosensitive silane coupling agent according to the present invention will now be described in more detail based on the drawings.

FIGS. 1A, 1B, 1C and 1D are a process chart illustrating one embodiment of a method for forming a pattern using the photosensitive silane coupling agent according to the present invention.

The photosensitive silane coupling agent according to the present invention is immobilized on a substrate via a chemical bond. The substrate can be selected depending on the desired device, and may be, for example, a metal substrate, a semiconductor substrate, an insulating substrate such as glass, quartz, BN or the like, or may be a substrate having one or plural kinds of resist, spin-on-glass, metal, oxide, nitride or the like formed as a film on such substrates. Preferably, a hydroxyl group is formed on the surface of the substrate for immobilizing the photosensitive silane coupling agent.

To form a hydroxyl group on the substrate surface, it is preferable to perform pre-treatment of the substrate as necessary. The pre-treatment can be carried out by exposing the substrate surface to an acidic solution or a UV ray-ozone atmosphere. Examples of the acidic solution include sulfuric acid, hydrochloric acid, nitric acid, hydrogen peroxide and the like. These may be used alone or in combination of two or more thereof. A combination of sulfuric acid and hydrogen peroxide is preferable. For pre-treatment of a silicon substrate, the combination of sulfuric acid and hydrogen peroxide is especially preferable. Means for performing the pre-treatment with an acidic solution include coating, spraying, dipping and the like.

The photosensitive silane coupling agent according to the present invention is coated onto the substrate 1 shown in FIG. 1A, which is then heated to form a photosensitive silane coupling agent layer 2 (FIG. 1B). Coating of the photosensitive silane coupling agent can be carried out using a solution of just the photosensitive silane coupling agent or a solution in which the photosensitive silane coupling agent is dissolved in an organic solvent, by dipping, spin coating, spray coating, vapor deposition or the like. In the present invention, dipping or spin coating are preferable. After coating the photosensitive silane coupling agent, it is preferable to appropriately heat the substrate so as to complete the reaction with the hydroxyl groups on the substrate. Heating can be conducted using heating means such as a hotplate, a hot-air drier or the like, at a temperature of 80 to 200° C., and more preferably 80 to 150° C. As a result of the above-described treatment, a monomolecular layer of the photosensitive silane coupling agent according to the present invention is formed.

Then, the thus-formed photosensitive silane coupling agent layer according to the present invention is exposed patternwise using a publicly known exposure apparatus (FIG. 1C). The radiation rays used for exposure can be appropriately selected from among visible light, UV rays, far ultraviolet rays, X-rays, electron beam, γ rays, molecular beam, ion beam and the like. Especially preferable are mercury lamp rays (wavelength of 436 nm, 405 nm, 365 nm and 254 nm), a KrF excimer laser beam (wavelength of 248 nm), an ArF excimer laser beam (wavelength of 193 nm), and a $F_2$ excimer laser beam (wavelength of 157 nm). In addition, far UV rays, such as extreme UV rays (EUV, wavelength of 13 nm), or an electron beam are also preferable. These radiation rays can be employed singly or in a plurality together. For the photosensitive silane coupling agent according to the present invention, when the secondary amino group is protected by a 2-nitrobenzyloxycarbonyl group, it is preferable to use UV rays having a wavelength of no greater than 313 nm. When it is protected by a 4,5-dimethoxy-2-nitrobenzyloxycarbonyl group, it is preferable to use UV rays having a wavelength of no greater than 405 nm.

For the exposure method, it is also preferable to use near-field light generated from a photomask which is provided with a shielding layer comprising an opening width narrower than the wavelength of the exposure light source. Since near-field light is not affected by the diffraction limit, a finer pattern can be achieved. As the radiation rays used for near-field light exposure, the above-described radiation rays can be employed. These radiation rays can be employed singly or in a plurality together. The exposure by near-field light is conducted by closely adhering the photomask shielding layer to the article to undergo exposure. A near-field light exposure apparatus is low cost as it does not require an accurate optical system or expensive light source, and is thus especially preferable in the present invention in terms of productivity.

According to the above-described exposure step, on the exposed portion 3 the secondary amino groups immobilized on the substrate are formed patternwise. Since secondary amino groups do not react with benzaldehyde compounds, the secondary amino groups on the exposed portion are not eliminated due to side reactions. It is thus possible to form a microparticle pattern having few defects without a rinse step after exposure. In FIG. 1C, reference numeral 4 denotes an unexposed portion.

After exposure is completed, the substrate is dipped in a colloidal solution in which microparticles are dispersed. As a result of this step, microparticles 5 selectively adhere to the exposed portion or unexposed portion of the substrate to form a microparticle pattern (FIG. 1D).

FIGS. 2A, 2B, 2C and 2D are a schematic diagram illustrating a pattern formed by selectively arranging microparticles only on an exposed portion or an unexposed portion.

The shape of the pattern may be an isolated dot pattern (FIG. 2A), wherein one microparticle is adhered per one location of microdot-shaped exposed portion or unexposed portion on the substrate 1; or an isolated line pattern (FIG. 2B), wherein the microparticles 5 are aligned in a narrow line pattern. The shape of the pattern may also be a closest packed pattern (FIG. 2C), wherein the microparticles 5 are arranged in a closest packed manner on the exposed portion 3 or unexposed portion which is broader than the size of the microparticle. The shape of the pattern may also be a random pattern (FIG. 2D), wherein the microparticles 5 are randomly arranged on the exposed portion 3 or unexposed portion which is broader than the size of the microparticle, with an interval of a certain length or larger between the microparticles as a result of the repulsive force therebetween. These patterns may be freely formed depending on the intended device. In addition, the patterns which are formed are not limited to those described above.

The microparticles have an average particle diameter in the range of at least 0.5 nm and at most 500 nm, and preferably in the range of at least 5 nm and at most 100 nm. While the kind of microparticle may be selected depending on the intended device, especially preferable are microparticles having a positive or a negative charge and microparticles having a carboxyl group or a carboxylic acid anhydride on a terminal thereof. For example, gold microparticles or gold nanorods have a negative charge, and thus form an electrostatic bond with the positively-charged amino groups in the exposed portion. Positively charged microparticles selectively adhere to the unexposed portion of the substrate. The carboxyl groups on the end of the microparticles and the amino groups on the surface of the substrate 1 are linked by ionic bonds (FIG. 3).

Figure 4:
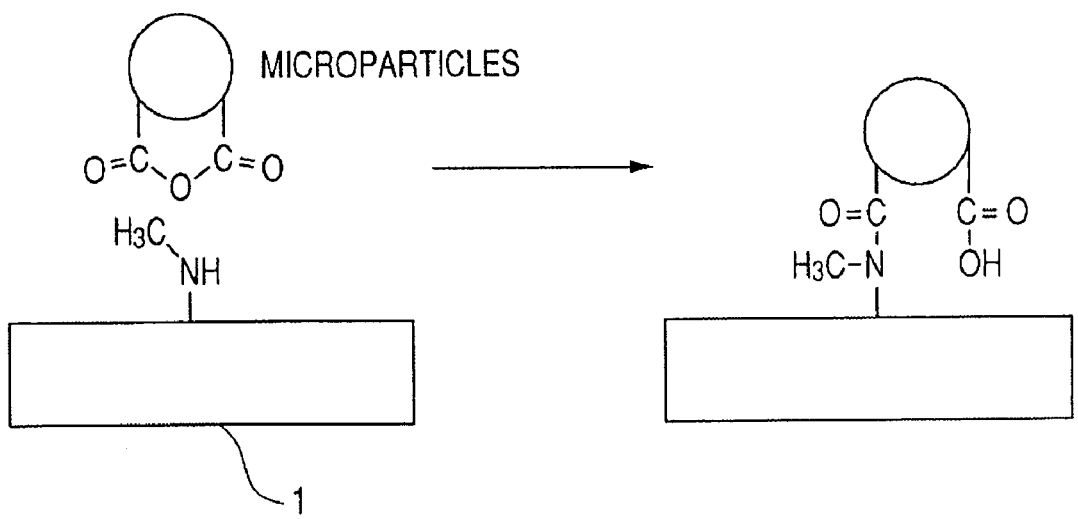
FIG. 4 is an explanatory diagram illustrating the bonding between a secondary amine group in the exposed portion of the substrate and an anhydrous carboxylic acid on the surface end of the microparticle.

The carboxylic acid anhydride on the end of the microparticles and the amino groups on the surface of the substrate 1 readily react at room temperature to form an amide bond so that they are strongly bonded (FIG. 4).

If it is intended to fabricate a single-electron device, microparticles are used which are conductive, such as those consisting of a metal or a metal oxide.

If it is intended to fabricate a magnetic recording medium, such as patterned media, magnetic metal microparticles are used, including Co, Ni, Fe, FePt, CoPt, CoNi, CoCr, CoP, CoNiP, FeCoB, FeCoNi, CoNiFeB, FeNi, FeCo, CoNiPt and the like.

If it is intended to fabricate a chemical sensor, metal microparticles are used. From the perspectives of sensitivity and chemical stability, noble metal microparticles are preferred, and gold microparticles or gold nanorods are especially preferred.

If it is intended to fabricate a quantum dot laser element, semiconductor microparticles, such as Si, SiGe, GaAs, InGaAs, GaN, InP, InAs, AlGaAs, InGaAsP, GaInAlP, InGaN, AlGaN and the like are used.

Figure 5A:
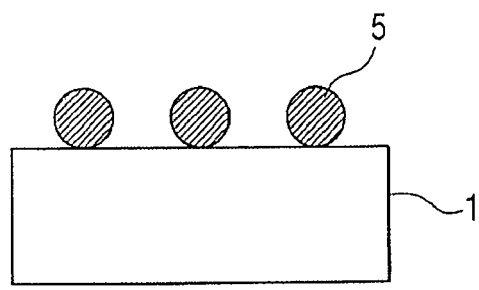
FIGS. 5A and 5B are an explanatory diagram illustrating a dry etching process with microparticles as a mask.
Figure 5B:
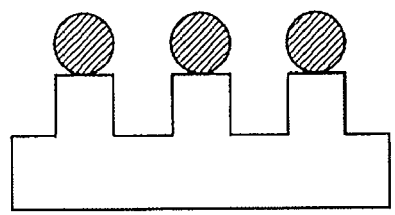

FIGS. 5A and 5B are an explanatory diagram illustrating a dry etching process with microparticles 5 as a mask. As illustrated in FIGS. 5A and 5B, the material of a substrate 1 may be processed with the microparticle pattern formed in the above-described manner as an etching mask to form a dot array pattern. In such a case, the substrate material is selected depending on the intended device.

If it is intended to fabricate a single-electron device, a metal or a metal oxide may be used as the substrate material.

If it is intended to fabricate a magnetic recording medium, such as patterned media, a magnetic metal including Co, Ni, Fe, FePt, CoPt, CoNi, CoCr, CoP, CoNiP, FeCoB, FeCoNi, CoNiFeB, FeNi, FeCo, CoNiPt and the like may be used.

If it is intended to fabricate a chemical sensor, from the perspectives of sensitivity and chemical stability, a noble metal is preferably used as the substrate material.

If it is intended to fabricate a quantum dot laser element, a semiconductor such as Si, SiGe, GaAs, InGaAs, GaN, InP, InAs, AlGaAs, InGaAsP, GaInAlP, InGaN, AlGaN or the like can be used as the substrate material.

Processing of the substrate can be carried out by dry etching using reactive plasma or radicals, ion milling or wet etching. Dry etching using reactive plasma is especially preferable, as such process is suitable for forming a pattern which is fine and has high verticality.

The dry etching gas is selected depending on the type of a substrate to be processed, and may be a plasma of a gas such as $CF_4$, $C_2F_6$, $C_3FB$, $CCl_2F_2$, $CCl_4$, $CBrF_3$, $BCl_3$, $PCl_3$, $SF_6$, $Cl_2$, HCl, HBr, $O_2$, $N_2$, Ar or the like.

Examples of wet etching agents include the following. Specifically, depending on the type of a material to be etched, examples include an aqueous solution of hydrofluoric acid, an aqueous solution of ammonium fluoride, an aqueous solution of phosphoric acid, an aqueous solution of acetic acid, an aqueous solution of nitric acid, an aqueous solution of ammonium cerium nitrate, an aqueous solution of potassium hydroxide, an aqueous solution of tetramethylammonium hydroxide and the like.

Figure 6A:
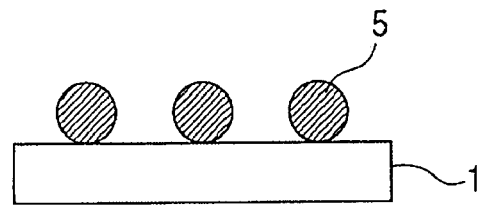
FIGS. 6A, 6B and 6C are an explanatory diagram illustrating a lift-off process with microparticles as a mask.
Figure 6B:
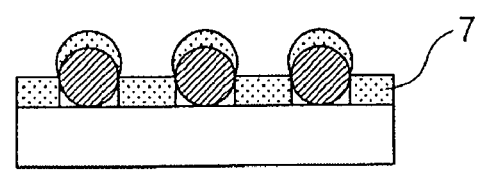
Figure 6C:
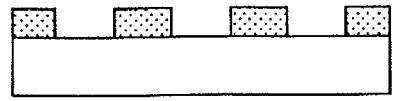

FIGS. 6A, 6B and 6C are an explanatory diagram illustrating a lift-off process with microparticles 5 as a mask. As illustrated in FIGS. 6A, 6B and 6C, a material layer 7 may be formed over the entire surface of the substrate 1 having a microparticle pattern formed as described above, and then the microparticles may be lifted off to form a hole array pattern of the desired material.

Examples of the material layer film formation method include various kinds of physical vapor deposition (PVD), chemical vapor deposition (CVD), and coating methods such as dipping, spin-coating and the like.

Specific examples of PVD methods include the following. Specific examples include various vacuum deposition methods such as electron beam heating, resistance heating, and flash evaporation, plasma deposition, bipolar sputtering, DC sputtering, DC magnetron sputtering, high-frequency sputtering, magnetron sputtering and the like. Further examples include various sputtering methods such as ion beam sputtering and bias sputtering, a DC (direct current) method, an RF method, a multi-cathode method, an activated reaction method, electric field deposition and the like. Other examples include various ion plating methods such as high-frequency ion plating, reactive ion plating and the like.

After film formation, the microparticles and the film adhered thereon are removed by dipping them into an organic solvent, an aqueous alkali solution, an aqueous acidic solution or the like. It is preferable to carry out heating, rocking and the like as necessary.

Various devices can be fabricated using the microparticle pattern, hole array pattern, or dot array pattern formed in the above-described manner.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-070002, filed Mar. 14, 2006, which is hereby incorporated by reference in its entirety.

What is claimed is:

1. A photosensitive silane coupling agent having a structure represented by the following general formula (1),

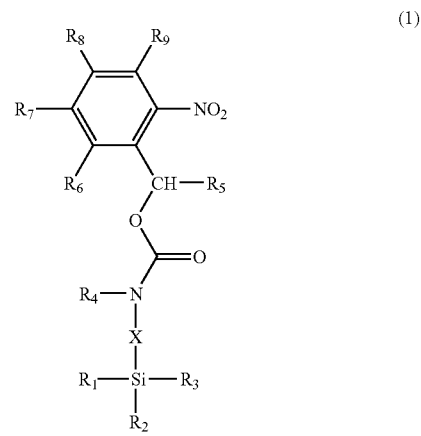

wherein X is a polymethylene group part of hydrogen atoms of which may be substituted with a fluorine atom or an alkyl group, a phenylene group part of hydrogen atoms of which may be substituted with a fluorine atom or an alkyl group, a naphthylene group part of hydrogen atoms of which may be substituted with a fluorine atom or an alkyl group, or a divalent group having a structure on which at least two of the polymethylene group, the phenylene group, and the naphthylene group are bonded to each other; at least one of $R_1$, $R_2$ and $R_3$ is an alkoxy group or a halogen atom, the other(s) being selected from the group consisting of an alkyl group, an alkenyl group and a hydrogen atom; $R_4$ is an alkyl group part of hydrogen atoms of which may be substituted with a fluorine atom, a phenyl group part of hydrogen atoms of which may be substituted with a fluorine atom or an alkyl group, or a naphthyl group part of hydrogen atoms of which may be substituted with a fluorine atom or an alkyl group; $R_5$ is a hydrogen atom or an alkyl group; and $R_6$, $R_7$, $R_8$ and $R_9$ are selected from the group consisting of a nitro group, a hydrogen atom, a halogen atom, an alkyl group, and an alkyl group or an alkoxy group part or the whole of hydrogen atoms of which are substituted with a fluorine atom.

2. A method of forming a microparticle pattern having a structure wherein a plurality of microparticles which have an average particle diameter of at least 0.5 nm and at most 500 nm are arranged on a substrate, the method comprising the steps of:

layering the photosensitive silane coupling agent according to claim 1 onto a surface of the substrate, exposing the photosensitive silane coupling agent patternwise, generating a carboxyl group on the photosensitive silane coupling agent layer in an exposed portion, and selectively arranging microparticles on the exposed portion or unexposed portion.

3. The method of forming a microparticle pattern according to claim 2, further comprising the step of processing the substrate by etching with the microparticle pattern as a mask.

4. The method of forming a microparticle pattern according to claim 2, further comprising the steps of forming a film over the entire substrate on which the microparticle pattern is formed, and forming a film pattern by removing the microparticle pattern and the film formed thereon.

5. The method of forming a microparticle pattern according to claim 2, wherein the microparticles are affanged by using a colloidal solution containing the microparticles.

6. The method of forming a microparticle pattern according to claim 2, wherein the exposure is caffied out using near-field light generated from a photomask which is provided with a light-shielding layer comprising an opening narrower than the wavelength of the exposure light source.

7. The method of forming a microparticle pattern according to claim 2, wherein the microparticles are formed of a material selected from the group consisting of metals, metal oxides, semiconductors and resins.

8. The method of forming a microparticle pattern according to claim 2, wherein the microparticles have an amino group on an end of the surface of the microparticles.

9. A method of fabricating a device using the method of forming a microparticle pattern according to claim 2.

10. The method of fabricating a device according to claim 9, wherein a single-electron device is fabricated by forming minute tunnel junction sites using said method of forming a microparticle pattern according to claim 2.

11. The method of fabricating a device according to claim 9, wherein a patterned medium is fabricated by forming a magnetic bit array using said method of forming a microparticle pattern according to claim 2.

12. The method of fabricating a device according to claim 9, wherein a chemical sensor is fabricated by forming a metallic microparticle pattern using said method of forming a microparticle pattern according to claim 2.

13. The method of fabricating a device according to claim 9, wherein a quantum dot laser element is fabricated by forming a quantum dot array structure using said method of forming a microparticle pattern according to claim 2.

14. The method of fabricating a device according to claim 9, wherein a photonic crystal optical device is fabricated by forming a two-dimensional photonic crystal structure using said method of forming a microparticle pattern according to claim 2.

* * * * *